US009867546B2

(12) United States Patent
Tzvieli et al.

(10) Patent No.: US 9,867,546 B2
(45) Date of Patent: Jan. 16, 2018

(54) WEARABLE DEVICE FOR TAKING SYMMETRIC THERMAL MEASUREMENTS

(71) Applicant: Facense Ltd., Kiryat Tivon (IL)

(72) Inventors: Arie Tzvieli, Berkeley, CA (US); Ari M Frank, Haifa (IL); Gil Thieberger, Kiryat Tivon (IL)

(73) Assignee: Facense Ltd., Kiryat Tivon (IL)

( * ) Notice: Subject to any disclaimer, the term of this patent is extended or adjusted under 35 U.S.C. 154(b) by 24 days.

(21) Appl. No.: 15/182,566

(22) Filed: Jun. 14, 2016

(65) Prior Publication Data

US 2016/0363483 A1    Dec. 15, 2016

Related U.S. Application Data

(60) Provisional application No. 62/175,319, filed on Jun. 14, 2015, provisional application No. 62/202,808, filed on Aug. 8, 2015.

(51) Int. Cl.
*G01J 5/12* (2006.01)
*A61B 5/01* (2006.01)
(Continued)

(52) U.S. Cl.
CPC ............ *A61B 5/015* (2013.01); *A61B 5/0075* (2013.01); *A61B 5/165* (2013.01); *A61B 5/6803* (2013.01); *A61B 5/6814* (2013.01); *A61B 5/7282* (2013.01); *A61B 5/748* (2013.01); *G01J 5/0265* (2013.01); *G01J 5/12* (2013.01); *A61B 5/0077* (2013.01); *A61B 2562/0271* (2013.01); *A61B 2562/0276* (2013.01); *A61B 2576/00* (2013.01);
(Continued)

(58) Field of Classification Search
CPC ..... A61B 5/015; A61B 5/0077; A61B 5/0075; A61B 5/6803; A61B 5/6814; A61B 5/7282; G01J 5/12; G01J 5/0265
See application file for complete search history.

(56) References Cited

U.S. PATENT DOCUMENTS 5,664,578 A   9/1997 Boczan
6,121,953 A   9/2000 Walker
(Continued)

OTHER PUBLICATIONS

Cardone, D., Pinti. P., & Merla. A. (2015). Thermal infrared imaging-based computational psychophysiology for psychometrics. Computational and mathematical methods in medicine, 2015.
(Continued)

*Primary Examiner* — David Porta
*Assistant Examiner* — Faye Boosalis
(74) *Attorney, Agent, or Firm* — Active Knowledge Ltd.

(57) ABSTRACT

Wearable devices for taking symmetric thermal measurements. One device includes first and second thermal cameras physically coupled to a frame worn on a user's head. The first thermal camera takes thermal measurements of a first region of interest that covers at least a portion of the right side of the user's forehead. The second thermal camera takes thermal measurements of a second ROI that covers at least a portion of the left side of the user's forehead. Wherein the first and second thermal cameras are not in physical contact with their corresponding ROIs, and as a result of being coupled to the frame, the thermal cameras remain pointed at their corresponding ROIs when the user's head makes angular movements.

20 Claims, 6 Drawing Sheets

(51) Int. Cl.
*A61B 5/16* (2006.01)
*A61B 5/00* (2006.01)
*G01J 5/02* (2006.01)
*G01J 5/00* (2006.01)

(52) U.S. Cl.
CPC ............... *G01J 2005/0077* (2013.01); *G01J 2005/0085* (2013.01)

(56) References Cited

U.S. PATENT DOCUMENTS

| | | | |
|---|---|---|---|
| 6,837,615 | B2 | 1/2005 | Newman |
| 6,996,256 | B2 | 2/2006 | Pavlidis |
| 7,027,621 | B1 | 4/2006 | Prokoski |
| 7,135,980 | B2 | 11/2006 | Moore et al. |
| 7,138,905 | B2 | 11/2006 | Pavlidis et al. |
| 8,149,273 | B2 | 4/2012 | Liu et al. |
| 8,289,443 | B2 | 10/2012 | MacKenzie |
| 8,334,872 | B2 | 12/2012 | Epps et al. |
| 8,360,986 | B2 | 1/2013 | Farag et al. |
| 8,573,866 | B2 | 11/2013 | Bond et al. |
| 8,585,588 | B2 | 11/2013 | Kovarik et al. |
| 8,723,790 | B1 | 5/2014 | Schaefer |
| 8,768,438 | B2 | 7/2014 | Mestha et al. |
| 8,786,698 | B2 | 7/2014 | Chen et al. |
| 8,855,384 | B2 | 10/2014 | Kyal et al. |
| 8,964,298 | B2 | 2/2015 | Haddick et al. |
| 9,019,174 | B2 | 4/2015 | Jerauld |
| 9,020,185 | B2 | 4/2015 | Mestha et al. |
| 9,194,749 | B2 | 11/2015 | Pompei |
| 9,211,069 | B2 | 12/2015 | Larsen et al. |
| 9,410,854 | B2 | 8/2016 | Padiy |
| 2002/0080094 | A1 | 6/2002 | Biocca et al. |
| 2003/0012253 | A1* | 1/2003 | Pavlidis ............ A61B 5/015 374/45 |
| 2005/0083248 | A1 | 4/2005 | Biocca et al. |
| 2005/0271117 | A1 | 12/2005 | Grassl et al. |
| 2007/0047768 | A1 | 3/2007 | Gordon et al. |
| 2007/0248238 | A1 | 10/2007 | Abreu |
| 2007/0265507 | A1 | 11/2007 | de Lemos |
| 2008/0260212 | A1 | 10/2008 | Moskal et al. |
| 2009/0221888 | A1 | 9/2009 | Wijesiriwardana |
| 2009/0237564 | A1 | 9/2009 | Kikinis et al. |
| 2010/0191124 | A1 | 7/2010 | Prokoski |
| 2010/0280334 | A1 | 11/2010 | Carlson et al. |
| 2012/0062719 | A1 | 3/2012 | Debevec et al. |
| 2012/0105473 | A1 | 5/2012 | Bar-Zeev et al. |
| 2012/0327194 | A1 | 12/2012 | Shiratori et al. |
| 2013/0116591 | A1* | 5/2013 | Heller ............... A61B 5/6887 600/549 |
| 2013/0215244 | A1 | 8/2013 | Mestha et al. |
| 2013/0230074 | A1* | 9/2013 | Shin .................. G01J 5/0025 374/129 |
| 2013/0257709 | A1 | 10/2013 | Raffle et al. |
| 2014/0180449 | A1 | 6/2014 | Sung |
| 2014/0347265 | A1 | 11/2014 | Aimone et al. |
| 2015/0087924 | A1 | 3/2015 | Li et al. |
| 2015/0126872 | A1* | 5/2015 | Dubielczyk ........ A61B 5/0077 600/473 |
| 2015/0157255 | A1 | 6/2015 | Nduka |
| 2015/0297126 | A1 | 10/2015 | Atsumori et al. |
| 2015/0310263 | A1 | 10/2015 | Zhang et al. |
| 2016/0015289 | A1 | 1/2016 | Simon et al. |
| 2016/0081622 | A1 | 3/2016 | Abreu |
| 2016/0091877 | A1 | 3/2016 | Fullam et al. |
| 2016/0098592 | A1 | 4/2016 | Lee et al. |
| 2016/0100790 | A1 | 4/2016 | Cantu et al. |
| 2016/0216760 | A1 | 7/2016 | Trutna et al. |

OTHER PUBLICATIONS

Hawkes, P. W. (2012). Advances in Imaging and Electron Physics (vol. 171). Academic Press. Chapter 2.

Mizuno, T., & Kume, Y. (Aug. 2015). Development of a Glasses-Like Wearable Device to Measure Nasal Skin Temperature. In International Conference on Human-Computer Interaction (pp. 727-732). Springer International Publishing.

Ioannou, S., Gallese, V., & Merla, A. (2014). Thermal infrared imaging in psychophysiology: potentialities and limits. Psychophysiology, 51(10), 951-963.

Fernández-Cuevas, I., Marins, J. C. B., Lastras, J. A., Carmona, P. M. G., Cano, S. P., García-Concepción, M. Á., & Sillero-Quintana, M. (2015). Classification of factors influencing the use of infrared thermography in humans: A review. Infrared Physics & Technology, 71, 28-55.

Jenkins, S. D., & Brown. R. D. H. (2014). A correlational analysis of human cognitive activity using Infrared Thermography of the supraorbital region, frontal EEG and self-report of core affective state. QIRT.

Johnson, M. L., Price, P. A., & Jovanov, E. (Aug. 2007). A new method for the quantification of breathing. In Engineering in Medicine and Biology Society, 2007. EMBS 2007. 29th Annual. International Conference of the IEEE (pp. 4568-4571). IEEE.

Lewis, G. F., Gatto. R. G., & Porges, S. W. (2011). A novel method for extracting respiration rate and relative tidal volume from infrared thermography. Psychophysiology, 48(7), 877-887.

Carine Collé, Re-Experience Big-Data, 3 months group project with Sanya Rai Gupta and Florian Puech, UK, London, RCA, IDE, 2014, Amoeba.

Fei, J., & Pavlidis, I. (Aug. 2006). Analysis of breathing air flow patterns in thermal imaging. In Engineering in Medicine and Biology Society, 2006. EMBS'06. 28th Annual International Conference of the IEEE (pp. 946-952). IEEE.

Nhan, B. R., & Chau, T. (2010). Classifying affective states using thermal infrared imaging of the human face. IEEE Transactions on Biomedical Engineering, 57(4), 979-987.

Appel, V. C., Belini, V. L., Jong, D. H., Magalhães, D. V., & Caurin, G. A. (Aug. 2014). Classifying emotions in rehabilitation robotics based on facial skin temperature. In Biomedical Robotics and Biomechatronics (2014 5th IEEE RAS & EMBS International Conference on (pp. 276-280). IEEE.

Ramirez, G. A., Fuentes, O., Crites Jr, S. L., Jimenez, M., & Ordonez, J. (2014). Color analysis of facial skin: Detection of emotional state. In Proceedings of the IEEE Conference on Computer Vision and Pattern Recognition Workshops (pp. 468-473).

Cross, C. B., Skipper, J. A., & Petkic, D. (May 2013). Thermal imaging to detect physiological indicators of stress in humans. In SPIE Defense. Security, and Sensing (pp. 870501-870501). International Society for Optics and Photonics.

Treacy Solovey, E., Afergan, D., Peck, E. M., Hincks, S. W., & Jacob, R. J. (2015). Designing implicit interfaces for physiological computing: Guidelines and lessons learned using fNIRS. ACM Transactions on Computer-Human Interaction (TOCHI), 21(6), 35.

Bernardi, L., Wdowczyk-Szulc. J., Valenti, C., Castoldi, S., Passino, C., Spadacini. G., & Sleight, P. (2000). Effects of controlled breathing, mental activity and mental stress with or without verbalization on heart rate variability. Journal of the American College of Cardiology, 35(6), 1462-1469.

Choi, J. S., Bang, J. W., Heo, H., & Park, K. R. (2015). Evaluation of Fear Using Nonintrusive Measurement of Multimodal Sensors. Sensors, 15(7), 17507-17533.

Kimura, S., Fukuomoto, M., & Horikoshi, T. (Sep. 2013). Eyeglass-based hands-free videophone. In Proceedings of the 2013 International Symposium on Wearable Computers (pp. 117-124). ACM.

Romera-Paredes, B., Zhang, C., & Zhang, Z. (Jul. 2014). Facial expression tracking from head-mounted, partially observing cameras. In Multimedia and Expo (ICME), 2014 IEEE International Conference on (pp. 1-6). IEEE.

Mizuno, T., Sakai, T., Kawazura, S., Asano, H., Akehi, K., Matsuno, S., . . . & Itakura, N. (Jul. 2015). Facial Skin Temperature Fluctuation by Mental Work-Load with Thermography. In the International Conference on Electronics and Software Science (ICESS2015) Proceedings (pp. 212-215).

Hong, K., Yuen, P., Chen, T., Tsitiridis, A., Kam, F., Jackman, J., . . . & Lightman+, F. T. S. (Sep. 2009). Detection and classification of stress using thermal imaging technique. In Proc. of SPIE Vol (vol. 7486, pp. 74860I-1).

(56) References Cited

OTHER PUBLICATIONS

Tsiamyrtzis, P., Dowdall, J., Shastri, D., Pavlidis, I. T., Frank, M. G., & Ekman, P. (2007). Imaging facial physiology for the detection of deceit. International Journal of Computer Vision, 71(2), 197-214.
Clay-Warner, J., & Robinson, D. T. (2015). Infrared thermography as a measure of emotion response. Emotion Review, 7(2), 157-162.
Pavlidis, I., Dowdall, J., Sun, N.. Puri, C., Fci, J., & Garbcy, M. (2007). Interacting with human physiology. Computer Vision and Image Understanding, 108(1), 150-170.
Sharma, N.. Dhall. A., Gedeon, T., & Goecke, R. (Sep. 2013). Modeling stress using thermal facial patterns: A spatio-temporal approach. In Affective Computing and Intelligent Interaction (ACII), 2013 Humaine Association Conference on (pp. 387-392). IEEE.
Nagaraj, S.. Quoraishee, S., Chan, G.. & Short. K. R. (Apr. 2010). Biometric study using hyperspectral imaging during stress. In SPIE Defense, Security, and Sensing (pp. 76740K-76740K). International Society for Optics and Photonics.
Murthy. R., & Pavlidis. I. (2006). Noncontact measurement of breathing function. IEEE Engineering in Medicine and Biology Magazine, 25(3), 57-67.
Kurz, M., Hölzl. G., Riener, A., Anzengruber, B., Schmittner, T., & Ferscha, A. (Sep. 2012). Are you cool enough for Texas Hold'Em Poker?. In Proceedings of the 2012 ACM Conference on Ubiquitous Computing (pp. 1145-1149). ACM.
Shastri, D., Papadakis, M., Tsiamyrtzis, P., Bass, B., & Pavlidis. I. (2012). Perinasal imaging of physiological stress and its affective potential. IEEE Transactions on Affective Computing, 3(3), 366-378.
Daniel Afergan, Samuel W. Hincks, Tomoki Shibata, and Robert J.K. Jacob, Phylter: A System for Modulating Notications in Wearables Using Physiological Sensing.
Horikoshi, T. (2014). Prototype Glasses-type Device with Videophone Capabilities—Hands-free Videophone.
Boccanfuso, L., & O'Kane, J. M. (Jun. 2012). Remote measurement of breathing rate in real time using a high precision, single-point infrared temperature sensor. In Biomedical Robotics and Biomechatronics (BioRob), 2012 4th IEEE RAS & EMBS International Conference on (pp. 1704-1709). IEEE.
Al-Khalidi, F. Q., Saatchi, R., Burke, D., Elphick, H., & Tan, S. (2011). Respiration rate monitoring methods: A review. Pediatric pulmonology, 46(6), 523-529.
Puri, C., Olson, L., Pavlidis, I., Levine, J., & Starren, J. (Apr. 2005). StressCam: non-contact measurement of users' emotional states through thermal imaging. In CHI'05 extended abstracts on Human factors in computing systems (pp. 1725-1728). ACM.
Merla, A. (2014). Thermal expression of intersubjectivity offers new possibilities to human-machine and technologically mediated interactions.
Rajoub, B. A., & Zwiggelaar, R. (2014). Thermal facial analysis for deception detection. IEEE transactions on information forensics and security, 9(6), 1015-1023.
Pavlidis, I., & Levine. J. (2002). Thermal image analysis for polygraph testing. IEEE Engineering in Medicine and Biology Magazine, 21(6), 56-64.
Sharma, N., Dhall, A., Gedeon, T., & Goecke, R. (2014). Thermal spatio-temporal data for stress recognition. EURASIP Journal on Image and Video Processing, 2014(1), 28.
Fei, J., & Pavlidis, I. (2010). Thermistor at a distance: unobtrusive measurement of breathing. IEEE Transactions on Biomedical Engineering, 57(4), 988-998.
Jovanov, E., Raskovic, D., & Hormigo, R. (2001). Thermistor-based breathing sensor for circadian rhythm evaluation. Biomedical sciences instrumentation, 37, 493-498.
Murthy, R., Pavlidis, I., & Tsiamyrtzis, P. (Sep. 2004). Touchless monitoring of breathing function. In Engineering in Medicine and Biology Society, 2004. IEMBS'04. 26th Annual International Conference of the IEEE (vol. 1, pp. 1196-1199). IEEE.
Yang, M., Liu. Q., Turner, T., & Wu, Y. (Jun. 2008). Vital sign estimation from passive thermal video. In Computer Vision and Pattern Recognition, 2008. CVPR 2008. IEEE Conference on (pp. 1-8). IEEE.

\* cited by examiner

WEARABLE DEVICE FOR TAKING SYMMETRIC THERMAL MEASUREMENTS

TECHNICAL FIELD

This application relates to wearable head mounted devices that include thermal cameras for taking symmetric thermal measurements.

BACKGROUND

Many physiological responses are manifested in the temperatures (and changes to the temperatures) that are measured on various regions of the human face. For example, facial temperatures may help determine the amount of stress a person might be under or the level of concentration the person has at a given time. In another example, facial temperatures can help determine how a user feels, e.g., whether a user is nervous, calm, or happy.

Thus, monitoring and analyzing facial temperatures can be useful for many health-related and life-logging related applications. However, typically collecting such data over time, when people are going through their daily activities can be very difficult. Typically, collection of such data involves utilizing thermal cameras that are bulky, expensive and need to be continually pointed at a person's face. Additionally, due to the people's movements in their day-to-day activities, various complex image analysis procedures need to be performed (e.g., face tracking and registration) in order to collect the required measurements.

Therefore, there is a need for way to be able to collect measurements of facial temperatures, and/or changes to the facial temperatures, at various regions of a person's face. Preferably, the measurements need to be able to be collected over a long period of time, while the person may be performing various day-to-day activities.

SUMMARY

According to one embodiment, a system includes: first and second thermal cameras physically coupled to a frame configured to be worn on a user's head; the first thermal camera is configured to take thermal measurements of a first region of interest ($TH_{ROI1}$), wherein $ROI_1$ covers at least a portion of the right side of the user's forehead; and the second thermal camera is configured to take thermal measurements of a second ROI ($TH_{ROI2}$), wherein $ROI_2$ covers at least a portion of the left side of the user's forehead; wherein the first and second thermal cameras are not in physical contact with their corresponding ROIs, the overlap between $ROI_1$ and $ROI_2$ is below 80% of the smallest area from among the areas of $ROI_1$ and $ROI_2$, and as a result of being coupled to the frame, the thermal cameras remain pointed at their corresponding ROIs when the user's head makes angular movements.

According to another embodiment, a system includes: first and second thermal cameras physically coupled to a frame configured to be worn on a user's head; the first thermal camera is configured to take thermal measurements of a first region of interest ($TH_{ROI1}$), wherein $ROI_1$ covers at least a portion of the right side frontal superficial temporal artery of the user; and the second thermal camera is configured to take thermal measurements of a second region of interest ($TH_{ROI2}$), wherein $ROI_2$ covers at least a portion of the left side frontal superficial temporal artery of the user; wherein the first and second thermal cameras are not in physical contact with their corresponding ROIs, and as a result of being coupled to the frame, the thermal cameras remain pointed at their corresponding ROIs when the user's head makes angular movements.

According to still another embodiment, a system includes: first and second thermal cameras physically coupled to a frame configured to be worn on a user's head; the first thermal camera is configured to take thermal measurements of a first region of interest ($TH_{ROI1}$), wherein $ROI_1$ covers at least a portion of the right side superficial temporal artery of the user; and the second thermal camera is configured to take thermal measurements of a second region of interest ($TH_{ROI2}$), wherein $ROI_2$ covers at least a portion of the left side superficial temporal artery of the user; wherein the first and second thermal cameras are not in physical contact with their corresponding ROIs, and as a result of being coupled to the frame, the thermal cameras remain pointed at their corresponding ROIs when the user's head makes angular movements.

BRIEF DESCRIPTION OF THE DRAWINGS

The embodiments are herein described by way of example only, with reference to the accompanying drawings. No attempt is made to show structural details of the embodiments in more detail than is necessary for a fundamental understanding of the embodiments. In the drawings.

DETAILED DESCRIPTION

Figure 1:
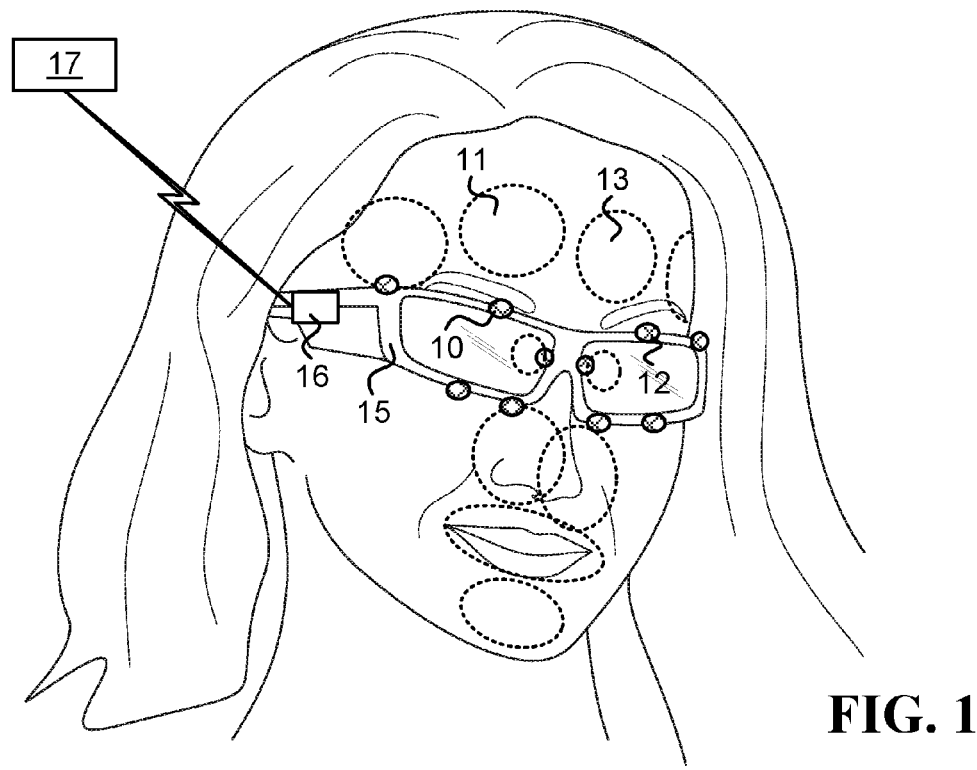
FIG. 1, FIG. 2, FIG. 3, and FIG. 4 illustrate various types of head mounted systems with cameras thereon, wherein the dotted circles and ellipses illustrate the region of interests of the cameras.

The term "thermal camera", as used herein, refers to a non-contact device comprising a thermal sensor useful for measuring wavelengths longer than 2500 nm. The thermal sensor may be used to measure spectral radiation characteristics of a black body at the user's body temperatures (around 310 K) according to Planck's radiation law. Although the thermal camera may also measure wavelengths shorter than 2500 nm, a camera that measures near-IR (such as 700-1200 nm), and is not useful for measuring wavelengths longer than 2500 nm, is referred to herein as near-IR camera and is not considered herein a thermal camera because it typically may not be used to effectively measure black body temperatures around 310 K. A thermal camera may include one or more sensors, where each sensor may include one or more sensing elements (that also referred to as pixels). For example, a thermal camera may include just one sensing element (i.e., one pixel, such as one thermopile sensor or one pyroelectric sensor), or a matrix containing thousands or even millions of pixels (such as a vector or a matrix of uncooled bolometer sensing elements). When a thermal capturing device utilizes optics for its operation, then the term "thermal camera" may refer to the optics (e.g., one or more lenses). When a thermal capturing device includes an optical limiter that limits the angle of view (such as in a pinhole camera, or a thermopile sensor inside a standard TO-5, TO-18, or TO-39 package with a window, or a thermopile sensor with a polished metal field limiter), then the term "thermal camera" may refer to the optical limiter. "Optical limiter" may also be referred to herein as a "field limiter" or "field of view limiter". Optionally, the field limiter may be made of a material with low emissivity and small thermal mass, such as Nickel-Silver and/or Aluminum foil.

The term "thermal camera" may also refer to a readout circuit adjacent to the thermal sensor, and may also include housing that holds the thermal sensor.

The term "thermal measurements of ROI" (usually denoted $TH_{ROI}$) may refer to at least one of the following: (i) "temperature measurements of ROI" (usually denoted $T_{ROI}$) taken for example with a thermopile sensor or a bolometer sensor which measure the temperature at the ROI, and (ii) "temperature change measurements of ROI" (usually denoted $\Delta T_{ROI}$) taken for example with a pyroelectric sensor that measures the temperature change at the ROI, or by watching the change in the measurements taken at different times by a thermopile sensor or a bolometer sensor.

Sentences such as "the thermal camera does not touch the ROI" specifically indicate that the thermal camera is not in contact with the user's skin, meaning that in a nominal operating condition there should be a space of at least 1 mm between the thermal camera (including its optics and housing) and the user's skin.

The term "circuit" is defined herein as an electronic device, which may be analog and/or digital, such as one or more of the following: an amplifier, a differential amplifier, a filter, analog and/or digital logic, a processor, a controller, a computer, an ASIC, and an FPGA.

Known systems for analyzing facial cues based on temperature measurements receive series of thermal images composed of pixels that represent temperature (T) measurements. Measuring the temperature is required in order to run a tracker and perform image registration, which compensate for the movements of the user in relation to the thermal camera and brings the images into precise alignment for analysis and comparison.

In one embodiment, a thermal camera (also referred to as a thermal sensor) is coupled to a frame worn on a user's head. In this configuration, the thermal camera moves with the user's head when the head changes its location and orientation in space, and thus there may be no need for a tracker and/or there may be no need for image registration. As a result, it is possible to run the image processing and/or signal processing algorithms on the series of thermal differences ($\Delta T$) measured by each thermal sensing element. Running the image/signal processing algorithms on the measured $\Delta T$ increases the accuracy of the system significantly compared to the case where $\Delta T$ is derived from images/signals representing temperature measurements (T).

Optionally, the temperature change at the ROI over time ($\Delta T_{ROI}$) is analyzed in relation to another parameter, such as the stimulus the user is exposed to, and/or other physiological measurements (such as EEG, skin conductance, pulse, breathing rate, and/or blood pressure).

Examples of thermopile sensors that may be useful for at least some of the embodiments herein include Texas Instruments "TMP006B Infrared Thermopile Sensor in Chip-Scale Package", Melexis "MLX90614 family Single and Dual Zone Infra-Red Thermometer in TO-39", HL-Planartechnik GmbH "TS118-3 thermopile sensor", Dexter Research Center, Inc. "DX-0875 detector", Dexter Research Center, Inc. "Temperature Sensor Module (TSM) with ST60 thermopile and onboard ASIC for amplification, digitizing, temperature compensation and calibration". When it is assumed that the sensor keeps measuring the same area on the object, these examples of thermopile sensors can provide readings of $\Delta T$, where often the measurement error of $\Delta T$ is much smaller than the measurement error of T. Therefore, maintaining the thermal camera pointed at the ROI, also when the user's head makes angular movements, enables at least some of the embodiments to utilize the more accurate $\Delta T$ measurement to identify fine cues that may not be identified based on image processing of temperature measurements (T) received from a camera that is not continuously pointed at the ROI (assuming sensors with same characteristics are used in both scenarios). In some embodiment, the performances of a thermopile and/or bolometer sensors may be improved using techniques such as described in U.S. Pat. No. 6,129,673.

In some embodiments, a thermal camera comprises a thermopile sensor configured to provide temperature readings in frequency below a frequency selected from the group of: 15 Hz, 10 Hz, 5 Hz, and 1 Hz.

In some embodiments, the field of view of the thermal camera is limited by a field limiter. For example, the thermal camera may be based on a Texas Instruments TMP006B IR thermopile utilizing a thin polished metal field limiter, or based on Melexis MLX90614 IR thermometers in TO-39 package. It is to be noted that the weight of the TMP006B or MLX90614 based thermal cameras is below 2 g, each.

For a better understanding of some of the disclosed embodiments, and not because the following theoretical discussion is necessary to make and/or use the disclosed embodiments, the following non-limiting theoretical discussion explains why the accuracy of the object temperature change ($\Delta T$) readings is expected to often be better than the accuracy of the object temperature (T) readings when dealing with sensors that measure temperature, such as thermopiles. If the following theoretical discussion is inaccurate then it should be disregarded and it is not to limit the scope of the disclosed embodiments in any way.

One problem with thermometers is that object temperature is hard to measure. Exact sensor output for a given object's temperature depends on properties of each particular sensing pixel, where each sensing pixel of the same sensor model may have its unique zero point, unique nonlinear coefficients, and unique electrical properties. However, when it comes to a very small change in object temperature, such as from 35.7 C to 35.9 C, then the zero point has a small impact when measuring difference between two readings, and the nonlinear effects is small since the difference itself is small. For example, although the uniformity of different Texas Instruments TMP006B infrared thermopile sensors is usually not good, the response of each particular sensor is quite linear and stable, meaning that with proper calibration and filtering, it is possible to achieve 0.1 C temperature difference precision, or even better.

Accuracy of a matrix of sensing pixels is given in terms of temperature accuracy. For example, accuracy of 0.2 C means that any pixel in the matrix will provide the same ±0.2 C temperature for a given object. However, when the current reading of a certain pixel is compared to its previous readings (as opposed to the case where the current reading of the certain pixel is compared to previous readings of other pixels), then the variability between the pixels essentially does not affect the accuracy of $\Delta T$ obtained from the certain pixel. For example, Micro80P Thermal Imaging Sensor, manufactured by Sofradir-EC, has an Array Uniformity <1.5% deviation; this large array uniformity may not affect the accuracy of ΔT obtain from a certain pixel in the unique case where the certain pixel remains pointed at the ROI also when the user's head makes angular movements.

The specific detectivity, noted as D*, of bolometers and thermopiles depends on the frequency of providing the temperature readings. In some embodiments, there is essentially no need for tracking and/or image registration, thus it is possible to configure the thermopile to provide temperature readings in frequencies such as 15 Hz, 10 Hz, 5 Hz, and even 1 Hz or lower. A thermopile with reaction time around 5-10 Hz may provide the same level of detectivity as a bolometer, as illustrated for example in the publication Dillner, U., Kessler, E., & Meyer, H. G. (2013), "Figures of merit of thermoelectric and bolometric thermal radiation sensors", J. Sens. Sens. Syst, 2, 85-94. In some cases, operating at low frequencies provides benefits that cannot be achieved when there is a need to apply image registration and run a tracker, which may enable a reduction in price of the low frequency sensors that may be utilized.

In some embodiments of thermopiles, there are many thermocouples where one side of each couple is thermally connected to a measuring membrane, while another is connected to the main body of the thermometer. In each thermocouple, a voltage dependent on temperature difference is generated according to Seebeck's effect. When these thermocouples are connected in series, the effect is multiplied by the number of thermocouples involved. For each thermocouple, the voltage generated is defined by Seebeck's formula: $dV=S*dT$, where dV is the generated voltage difference, dT is the temperature difference, and S is a Seebeck coefficient that is a material-dependent coefficient (for example 0.5 mV/K). Since accurate voltage measurement of several microvolts is achievable, this method may allow detection of ΔT at a resolution of 0.01K or less. Although, since a thermocouple senses the difference between two ends and not the object temperature, it is required to know the temperature of the main thermometer body with high precision, otherwise the precision drops. More information on Seebeck's effect and micromachined thermopiles can be found in the publication Graf, A., Arndt, M., & Gerlach, G. (2007), "Seebeck's effect in micromachined thermopiles for infrared detection. A review", Proc. Estonian Acad. Sci. Eng, 13(4), 338-353.

In some embodiments of bolometers, the measuring membrane is connected to a material that changes its resistance significantly when the temperature is changed as follows: $R=R0 (1+a*dT)$, where R is resistance at a given temperature, and R0 and 'a' are material-dependent parameters. In one example of vanadium pentoxide, the sensitivity highly depends on the layer creation technology, and the resistance change may be as high as 4% per Kelvin, where 2% may be a typical value. Since resistance value depends on the temperature, the measurements are theoretically independent of the temperature of the main thermometer body. However, in practice, there may be a heat flow between the measuring membrane and the main body, which imposes a practical limit on the maximum temperature difference. In addition, the maximum temperature difference may not be the same in both negative and positive directions, and with higher differences causing an increase in the measurement error.

Both bolometers and thermopiles work better when the object temperature is close to the detector temperature. Maintaining the temperature of the detector constant is helpful to detect small differences in object temperature precisely, thus, in one embodiment, the detectors are placed on a plate of metal having high thermal conductance, such as aluminum or copper, which optionally has Peltier elements and several high precision contact thermometers for temperature control.

Using several detectors instead of a single detector may decrease signal noise and increase stability. If the measurement electronics of a particular sensor has a long-term measurement drift (which may be added at on-chip circuit level), then using multiple sensors may be a practical way to remove the drift, such as in a small temperature-stabilized platform with several sensors.

When it comes to detection of differences in an object's temperature, often, one limitation is the ability to keep the sensors' temperature constant. At least with several relatively inexpensive commercially available sensors, temperature is measured with 0.01-0.02 C steps, meaning that even a single sensor may be able to detect ΔT of 0.04 C or less. However, for thermopile sensors, the detected signal is the difference between the object temperature and the thermometer case temperature, thus the case temperature needs to be measured with the appropriate precision. In one example, such high precision measurements may be obtained utilizing high quality temperature stabilization of the thermometer's base plate, which may require several high-precision contact thermometers and Peltier elements to control the temperature. In another example, the thermal camera uses bolometers, which are not so sensitive to case temperature, and enable operation in room temperature as long as the environment is maintained with no more than ±3 C changes.

Examples of pyroelectric sensors that may be useful for at least some of the embodiments herein include: (i) Excelitas Technologies analog pyroelectric non-contact sensor series, having one, two, four, or more elements; (ii) Excelitas Technologies DigiPyro® digital pyroelectric non-contact sensor series, having two, four, or more elements; and (ii) Murata Manufacturing Co., Ltd. dual type pyroelectric infrared sensor series, or Parallel Quad Type Pyroelectric Infrared Sensor Series.

In some embodiments, as a result of being physically coupled to the frame, a thermal camera remains pointed at the ROI when the user's head makes angular movements. It is to be noted that sentences such as "the thermal camera is physically coupled to the frame" refers to both direct physical coupling to the frame, which means that the thermal camera is fixed to/integrated into the frame, and indirect physical coupling to the frame, which means that the thermal camera is fixed to/integrated into an element that is physically coupled to the frame. In both the direct and indirect physical coupling embodiments, the thermal camera remains pointed at the ROI when the user's head makes angular movements. In some examples, the rate of angular movement referred to in sentences such as "when the user's head makes angular movements" is above 0.02 rad/sec, 0.1 rad/sec, or 0.4 rad/sec. Moreover, sentences such as "the thermal camera . . . is not in physical contact with the ROI" mean that the thermal camera utilizes a non-contact sensor that does not touch the ROI directly in a manner similar to a thermistor that needs to be in physical contact with the ROI in order to measure the ROI.

In some embodiments, a thermal camera may comprise an uncooled thermal sensor. Herein, an uncooled thermal sensor refers to a sensor useful for measuring wavelengths longer than 2500 nm, which: (i) operates at ambient temperature, or (ii) is stabilized at a temperature that is no more than ±20 Celsius from the ambient temperature. Optionally, the thermal camera utilizes for its operation a thermopile sensor. The reference Pezzotti, G., Coppa, P., & Liberati, F.

(2006), "Pyrometer at low radiation for measuring the forehead skin temperature", Revista Facultad de Ingeniería Universidad de Antioquia, (38), 128-135 describes one example of measuring the forehead temperature with a thermopile that provides accuracy better than 0.2 C, without necessitating physical contact with the forehead, and with a working distance between 350 and 400 mm. The optics in this example involves a single aspherical mirror, which may, or may not, be necessary when the thermal camera is located just a few centimeters from the ROI.

In some embodiments, a thermal camera utilizes for its operation at least one of the following uncooled thermal sensors: a bolometer sensor, a pyroelectric sensor, and a ferroelectric sensor. In other embodiments, a thermal camera comprises a cool thermal sensor.

For various purposes, thermal cameras may be positioned in certain locations, e.g., in order to be able to take measurements of a certain region of interest (ROI). Optionally, in order to provide useful measurements a thermal camera may be located away from a specific region, such as being located outside of the exhale streams of the mouth and nostrils. Herein, sentences such as "located outside the exhale streams of the mouth and nostrils" means located outside most of the normally expected exhale stream of the mouth and located outside most of the normally expected exhale streams from the nostrils. The normally expected exhale streams are determined according to a normal human who breathes normally, when having a relaxed (neutral) face, and when the neck, jaw, and facial muscles are not stretched nor contracted. For example, a thermal camera is considered to be located outside the exhale streams from the nostrils when it is located to the right of the right nostril, and/or to the left of the left nostril, and/or outside a 3D rectangle that extends from below the tip of the nose to the lower part of the chin with a base size of at least 4×4 cm. In another example, a thermal camera is considered to be located outside the exhale stream of the mouth when it is located outside a horizontal cylinder having height of 10-20 cm and diameter of 4-10 cm, where the top of the cylinder touches the base of the nose.

In the case of a thermal camera based on a thermal sensor such as a thermopile, the thermopile's reference junctions may compensate for changes in the temperature of the ROI. If the reference junction temperature is fixed, for example by placing the junctions over a heat sink and/or insulating them, then exhale streams from the nostrils and/or mouth may not affect the temperature difference between the ROI and the sensing junctions. However, when the reference junction temperature is not fixed, then the breath passing over the sensor may change the reading of the thermopile merely because the exhale stream is close to body temperature. For example, if the thermopile was at room temperature and the temperature of the reference junctions is essentially fixed, then the thermopile would register a voltage that is proportional to a change to the temperature between ROI and room temperature. However, if the sensing junctions are exposed to the exhale stream, then the thermopile may measure a wrong temperature of the ROI. In order to avoid such an error, in one embodiment a non-well isolated thermal camera is located outside the exhale streams, which means that the thermal camera is not placed in front of the nostrils and/or in front of the mouth, but to the side, above, below, and/or in any other possible location that is away from the nostrils and the mouth. In some embodiments, an additional thermal camera may be located inside the exhale streams from at least one of the mouth and the nostrils.

In one example, "a frame configured to be worn on the user's head" is interpreted as a frame that loads more than 50% of its weight on the user's head. For example, the frame in Oculus Rift and HTC Vive includes the foam placed on the user's face and the straps; the frame in Microsoft HoloLens includes the adjustment wheel in the headband placed on the user's head. In another example, "a frame configured to be worn on the user's head" may be an eyeglasses frame, which holds prescription and/or UV-protective lenses.

In one example, wide angular movements are interpreted as angular movements of more than 45 degrees. In one example, the locations of the first and second cameras relative to the user's head do not change even when the user's head performs wide angular and lateral movements, wherein wide angular and lateral movements are interpreted as angular movements of more than 60 degrees and lateral movements of more than 1 meter.

In one example, the frame is similar to extending side arms of eyeglasses. The frame may be positioned behind a user's ears to secure the HMS to the user. The frame may further secure the HMS to the user by extending around a rear portion of the user's head. Additionally or alternatively, the frame may connect to or be affixed within a head-mountable helmet structure.

The positions of the cameras on the figures are just for illustration. The cameras may be placed at other positions on the HMS. One of more of the visible light cameras may be configured to capture images at various resolutions or at different frame rates. Many video cameras with a small form-factor, such as those used in cell phones or webcams, for example, may be incorporated into some of the embodiments.

Further, illustrations and discussions of a camera represent one or more cameras, where each camera may be configured to capture the same view, and/or to capture different views (i.e., they may have essentially the same or different fields of view). In one embodiment, one or more of the cameras may include one or more elements, such as a gyroscope, an accelerometer, and/or a proximity sensor. Other sensing devices may be included within the camera, and/or in addition to the camera, and other sensing functions may be performed by one or more of the cameras.

In one embodiment, because facial structures may differ from user to user, the HMS may calibrate the direction, position, algorithms, and/or characteristics of one or more of the cameras and/or light sources based on the facial structure of the user. In one example, the HMS calibrates the positioning of a camera in relation to a certain feature on the user's face. In another example, the HMS changes, mechanically and/or optically, the positioning of a camera in relation to the frame in order to adapt itself to a certain facial structure.

Various systems described in this disclosure may include a display that is coupled to a frame worn on a user's head, e.g., a frame of a head-mounted system (HMS). In some embodiments, the display coupled to the frame is configured to present digital content to the user. Phrases in the form of "a display coupled to the frame" are to be interpreted as one or more of the following: (i) the frame can be worn and/or taken off together with the display such that when the user wears/takes off the HMS he/she also wears/takes off the display, (ii) the display is integrated with the frame, and optionally the display is sold together with the HMS, and/or (iii) the HMS and the display share at least one electronic element, such as a circuit, a processor, a memory, a battery, an optical element, and/or a communication unit for communicating with a non-head mounted computer.

Herein, a display may be any device that provides a user with visual images (e.g., text, pictures, and/or video). The images provided by the display may be two-dimensional or three-dimensional images. Some non-limiting examples of displays that may be used in embodiments described in this disclosure include: (i) screens and/or video displays of various devices (e.g., televisions, computer monitors, tablets, smartphones, or smartwatches), (ii) headset- or helmet-mounted displays such as augmented-reality systems (e.g., HoloLens), virtual-reality systems (e.g., Oculus rift, Vive, or Samsung GearVR), and mixed-reality systems (e.g., Magic Leap), and (iii) image projection systems that project images on a user's retina, such as Virtual Retinal Displays (VRD), which creates images by scanning low power laser light directly onto the retina.

In one embodiment, a helmet is coupled to the frame and configured to protect the user's scalp; wherein the helmet is selected from the group of: a sport helmet, a motorcycle helmet, a bicycle helmet, and a combat helmet. Phrases in the form of "a helmet coupled to the frame" are to be interpreted as one or more of the following: (i) the frame can be worn and/or take off together with the helmet such that when the user wears/takes off the helmet he/she also wears/takes off the HMS, (ii) the frame is integrated with the helmet and/or the helmet itself forms the frame, and optionally the HMS is sold together with the helmet, and/or (iii) the HMS and the helmet share at least one electronic element, such as an inertial measurement sensor, a circuit, a processor, a memory, a battery, an image sensor, and/or a communication unit for communicating with a non-head mounted computer.

In one embodiment, a brainwave headset is coupled to the frame and configured to collect brainwave signals of the user. Phrases in the form of "a brainwave headset coupled to the frame" are to be interpreted as one or more of the following: (i) the frame can be worn and/or take off together with the brainwave headset such that when the user wears/takes off the brainwave headset he/she also wears/takes off the HMS, (ii) the frame is integrated with the brainwave headset and/or the brainwave headset itself forms the frame, and optionally the HMS is sold together with the brainwave headset, and/or (iii) the HMS and the brainwave headset share at least one electronic element, such as an inertial measurement sensor, a circuit, a processor, a memory, a battery, and/or a communication unit.

FIG. 1, FIG. 2, FIG. 3, and FIG. 4 illustrate various types of head mounted systems with cameras thereon, wherein the dotted circles and ellipses illustrate the region of interests of the cameras. The cameras may be thermal cameras and/or visible light cameras.

Figure 5:
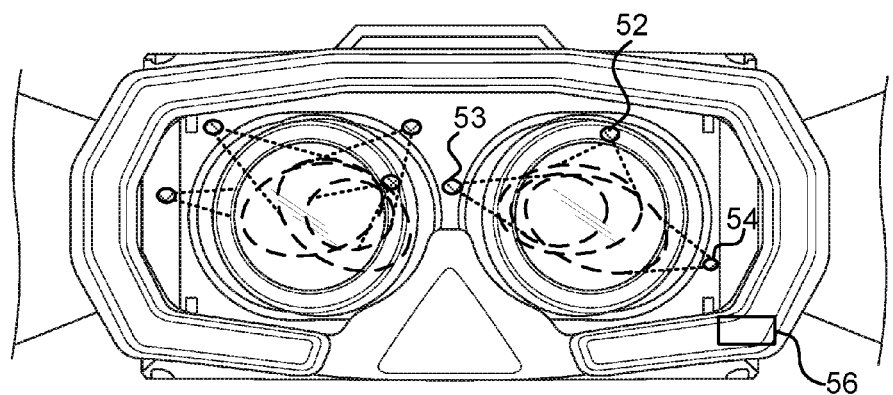
FIG. 5, FIG. 6, and FIG. 7 illustrate various potential locations to connect thermal cameras to various head mounted display frames in order to have at least some of the periorbital ROI within the field of view of one or more of the thermal cameras.
Figure 6:
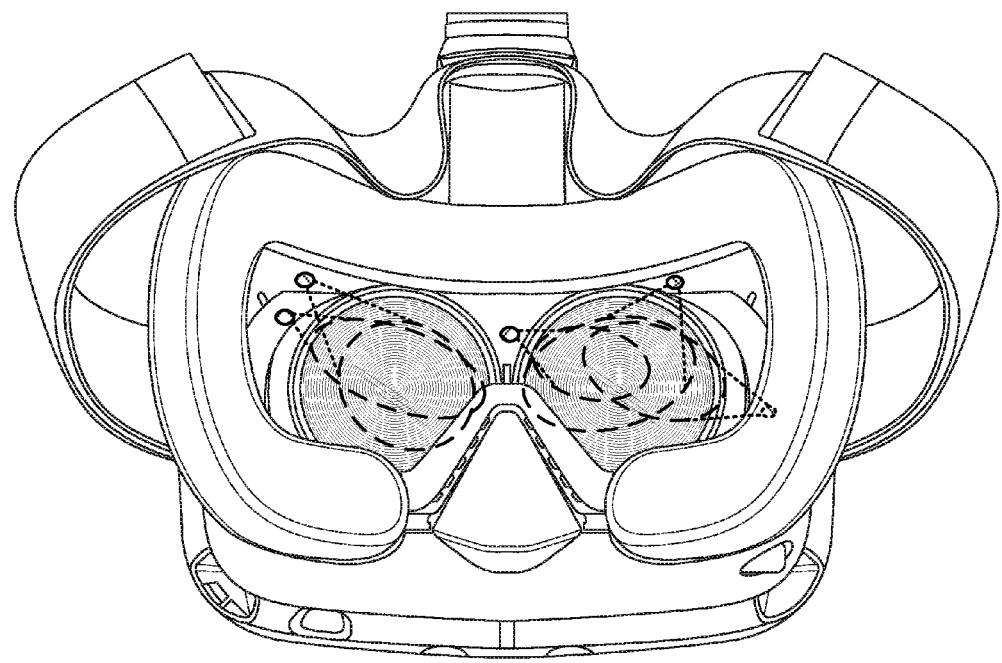
Figure 7:
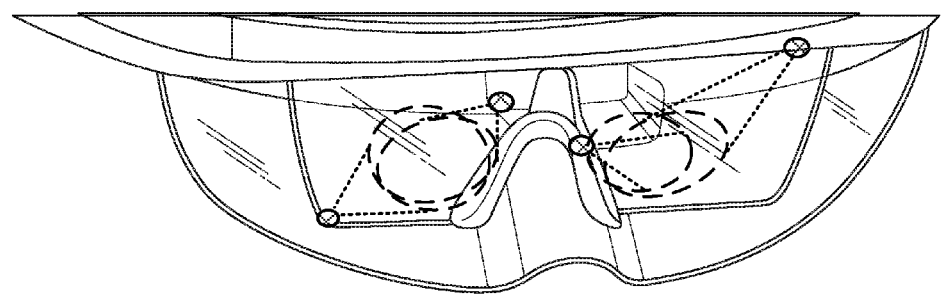

FIG. 5, FIG. 6, and FIG. 7 illustrate various potential locations to connect thermal cameras to various head mounted display frames in order to have at least some of the periorbital ROI within the field of view of one or more of the thermal cameras. Because the thermal cameras are located close to the ROI, they can be small, lightweight, and may be placed in many potential locations having line of sight to the respective ROIs.

Figure 9:
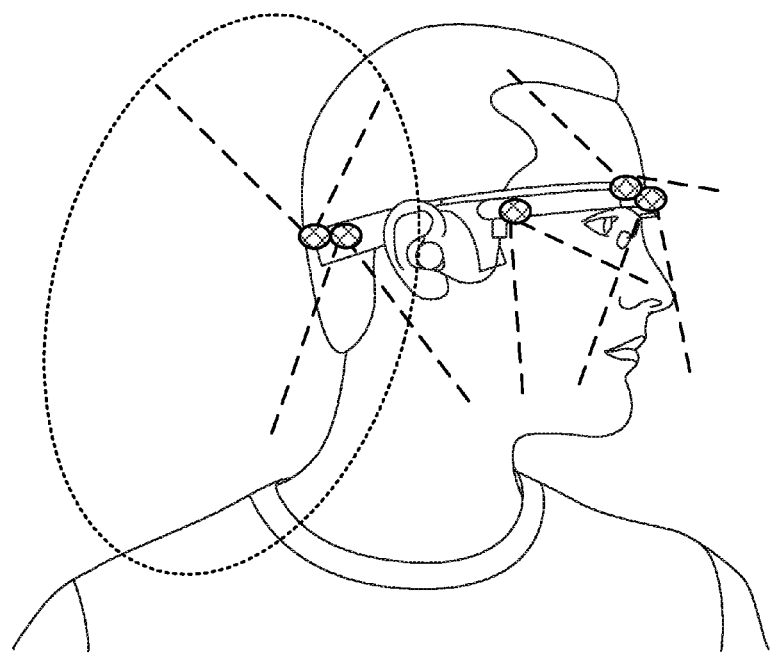
FIG. 9, FIG. 10, and FIG. 11 illustrate various types of head mounted systems with cameras thereon, wherein the dotted lines illustrate the fields of view of the cameras.
Figure 10:
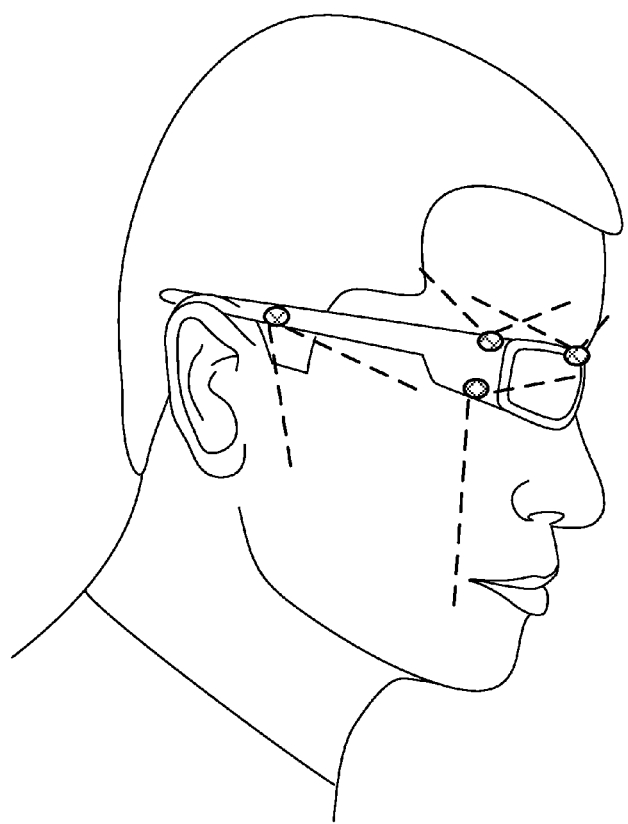
Figure 11:

FIG. 9, FIG. 10, and FIG. 11 illustrate various types of head mounted systems with cameras thereon, wherein the dotted lines illustrate the fields of view of the cameras. The cameras may be thermal cameras and/or visible light cameras.

As discussed above, collecting thermal measurements of various regions of a user's face can have many health-related (and other) applications. However, movements of the user and/or of the user's head can make acquiring this data difficult for many known approaches. To this end, some embodiments described herein utilize various combinations of thermal cameras that are coupled to a frame of a head-mounted system (also referred to as a "wearable system" or simply a "system"), as the descriptions of the following embodiments show.

FIG. 1 illustrates one embodiment of a system that includes a first thermal camera 10 and a second thermal camera 12 that are physically coupled to a frame 15 configured to be worn on a user's head. The first thermal camera is configured to take thermal measurements of a first region of interest 11 (the "first region of interest" denoted $ROI_1$, and the "thermal measurements of $ROI_1$" denoted $TH_{ROI1}$), where $ROI_1$ 11 covers at least a portion of the right side of the user's forehead, and the second thermal camera is configured to take thermal measurements of a second ROI ($TH_{ROI2}$), wherein $ROI_2$ 13 covers at least a portion of the left side of the user's forehead. The first thermal camera 10 is located below $ROI_1$ 11 and does not occlude $ROI_1$ 11. The second thermal camera 12 is located below $ROI_2$ 13 and does not occlude $ROI_2$ 13. Additionally, the first and second thermal cameras are not in physical contact with their corresponding ROIs, the overlap between $ROI_1$ and $ROI_2$ is below 80% of the smallest area from among the areas of $ROI_1$ and $ROI_2$, and as a result of being coupled to the frame, the thermal cameras remain pointed at their corresponding ROIs when the user's head makes angular movements.

In one embodiment, the system described above is configured to forward $TH_{ROI1}$ and $TH_{ROI2}$ to a processor 16 configured to identify a physiological response based on $TH_{ROI1}$ and $TH_{ROI2}$. The processor 16 may be located on the user's face, may be worn by the user, and/or may be located in a distance from the user, such as on a smartphone, a personal computer, a server, and/or on a cloud computer. The wearable processor 16 may communicate with the non-wearable processor 17 using any appropriate communication techniques.

Optionally, the physiological response identified by the processor (16 and/or 17) is indicative of at least one of the following: stress, mental workload, fear, sexual arousal, anxiety, pain, pulse, headache, and stroke.

In different embodiments, the ROIs mentioned above may cover slightly different regions on the user's face. In one example, the right side of the user's forehead covers at least 30% of $ROI_1$, and the left side of the user's forehead covers at least 30% of $ROI_2$. In another example, the right side of the user's forehead covers at least 80% of $ROI_1$, and the left side of the user's forehead covers at least 80% of $ROI_2$.

Measurements of the thermal cameras may be utilized for various calculations in different embodiments. For example, in one embodiment, the first and second thermal cameras measure temperatures at $ROI_1$ and $ROI_2$, respectively. In this embodiment, the system may further include a circuit configured to: receive a series of temperature measurements at $ROI_1$ and calculate temperature changes at $ROI_1$ ($\Delta T_{ROI1}$), receive a series of temperature measurements at $ROI_2$ and calculate temperature changes at $ROI_2$ ($\Delta T_{ROI2}$), and utilize $\Delta T_{ROI1}$ and $\Delta T_{ROI2}$ to identify a physiological response. Optionally, the system's nominal measurement error of the temperatures at $ROI_1$ is at least twice the system's nominal measurement error of the temperature changes at $ROI_1$ when the user's head makes angular movements above 0.02 rad/sec. Optionally, the system's nominal measurement error of the temperatures at $ROI_1$ is at least five time the system's nominal measurement error of the temperature changes at $ROI_1$ when the user's head makes angular movements above 0.2 rad/sec.

Following is a description of another embodiment of a system that includes thermal cameras that take measurements of other regions of a user's face.

In one embodiment, a system includes first and second thermal cameras physically coupled to a frame configured to be worn on a user's head. The first thermal camera is configured to take thermal measurements of a first region of interest ($TH_{ROI1}$), where $ROI_1$ covers at least a portion of the right side frontal superficial temporal artery of the user, and the second thermal camera is configured to take thermal measurements of a second region of interest ($TH_{ROI2}$), where $ROI_2$ covers at least a portion of the left side frontal superficial temporal artery of the user. Additionally, the first and second thermal cameras are not in physical contact with their corresponding ROIs, and as a result of being coupled to the frame, the thermal cameras remain pointed at their corresponding ROIs when the user's head makes angular movements.

In one embodiment, the system described above is configured to forward $TH_{ROI1}$ and $TH_{ROI2}$, to a processor configured to identify a physiological response based on $TH_{ROI1}$ and $TH_{ROI2}$. Optionally, the physiological response is indicative of the user's arterial pulse. Additionally or alternatively, the physiological response may be indicative of at least one of the following: stress, mental workload, fear, anxiety, pain, headache, and stroke.

In one example, the physiological signal (such as pulse or respiration) has periodic features, the thermal camera includes multiple sensing elements, and the computer may extract temporal signals for individual pixels inside $ROI_2$, and/or extract temporal signals for pixel clusters inside $ROI_2$, depending on the movement and the noise level. The calculation of the physiological signal may include harmonic analysis, such as a fast Fourier transform, to the temperature signal and/or temperature change signal of each pixel, or pixel clusters, over time in a sliding window, which may be followed by a non-linear filter to reduce low-frequency signal leakage in the measurement frequency range. In cases where some pixels may be less informative than others, a clustering procedure may be implemented to remove the outliers. Then the frequency peaks in the set of pixels of interest may be used to vote for the dominant frequency component, the bin with the most votes is selected as the dominant frequency, and the estimate of the physiological signal may be obtained from the median filtered results of the dominant frequency components in a small sliding window.

One example of a contact-free heart rate and respiratory rate detection through measuring infrared light modulation emitted near superficial blood vessels or a nasal area, respectively, is described in the reference Yang, M., Liu, Q., Turner, T., & Wu, Y. (2008), "Vital sign estimation from passive thermal video", In Computer Vision and Pattern Recognition, 2008. CVPR 2008. IEEE Conference on (pp. 1-8). IEEE. Pulsating blood flow induces subtle periodic temperature changes to the skin above the superficial vessels by heat diffusion, which may be detected by thermal video to reveal the associated heart rate. The temperature modulations may be detected through pixel intensity changes in the ROI using a thermal camera, and the corresponding heart rate may be measured quantitatively by harmonic analysis of these changes on the skin area above the superficial temporal artery (in this context, "the skin area above the artery" refers to "the skin area on top of the artery").

In one embodiment, because the thermal camera is coupled to the frame, challenges such as dealing with complications caused by movements of the user, ROI alignment, tracking based on hot spots or markers, and motion compensation in the IR video—are simplified, and maybe even eliminated.

The temperature modulation level due to blood pulsating is far less than normal skin temperature, therefore, in one embodiment, the subtle periodic changes in temperature are quantify based on frame differences. For example, after an optional alignment, the frame differences against a certain reference frame are calculated for every frame, based on corresponding pixels or corresponding pixel clusters. The temperature differences may look like random noise in the first several frames, but a definite pattern appears close to half of the pulse period; then the temperature differences become noisy again as approaching the pulse period. The heart rate is estimated by harmonic analysis of the skin temperature modulation above the superficial temporal artery. In one embodiment, a similar method is applied to respiration rate estimation by measuring the periodic temperature changes around the nasal area.

FIG. 7 in U.S. Pat. No. 8,360,986 to Farag et al illustrates the right and left frontal superficial temporal artery ROIs of one person. The locations and dimensions of the right and left frontal superficial temporal artery ROIs may change to some extent between different people. Due to the inherent benefits obtained from the disclosed head mounted thermal cameras, it may be enough that $ROI_1$ and $ROI_2$ cover just a portion of the right and left frontal superficial temporal artery ROIs. Additionally or alternatively, $ROI_1$ and $ROI_2$ may cover greater areas than the ROIs illustrated in FIG. 7 in U.S. Pat. No. 8,360,986.

The following is yet another description of an embodiment of a system that includes thermal cameras that take measurements of certain regions of a user's face. In one embodiment, a system includes first and second thermal cameras physically coupled to a frame configured to be worn on a user's head. The first thermal camera is configured to take thermal measurements of a first region of interest ($TH_{ROI1}$), where $ROI_1$ covers at least a portion of the right side superficial temporal artery of the user. The second thermal camera is configured to take thermal measurements of a second region of interest ($TH_{ROI2}$), where $ROI_2$ covers at least a portion of the left side superficial temporal artery of the user. Additionally, the first and second thermal cameras are not in physical contact with their corresponding ROIs, and as a result of being coupled to the frame, the thermal cameras remain pointed at their corresponding ROIs when the user's head makes angular movements.

In one embodiment, the system described above is configured to forward $TH_{ROI1}$ and $TH_{ROI2}$ to a processor configured to identify a physiological response based on $TH_{ROI1}$ and $TH_{ROI2}$. Optionally, the physiological response is indicative of the user's arterial pulse. Additionally or alternatively, the physiological response is indicative of at least one of the following: stress, mental workload, fear, anxiety, pain, headache, and stroke.

FIG. 7 in U.S. Pat. No. 8,360,986 to Farag et al illustrates the right and left superficial temporal artery ROIs of one person. The locations and dimensions of the right and left superficial temporal artery ROIs may change to some extent between different people. Due to the inherent benefits obtained from the disclosed head mounted thermal cameras, it may be enough that $ROI_1$ and $ROI_2$ cover just a portion of the right and left superficial temporal artery ROIs. Additionally or alternatively, $ROI_1$ and $ROI_2$ may cover greater areas than the ROIs illustrated in FIG. 7 in U.S. Pat. No. 8,360,986.

Yet another example of a system that includes thermal cameras that take measurements of certain regions of a user's face is given is the following description. In one embodiment, a wearable system configured to take thermal measurements that enable identification of a physiological response includes at least a frame and first, second, third, and fourth thermal cameras. The frame configured to be worn on a user's head, and the first, second, third and fourth thermal cameras remain pointed at their respective ROIs when the user's head makes angular movements.

The first and second thermal cameras, physically coupled to the frame, at locations to the right and to the left of the symmetry axis that divides the user's face to the right and left sides, respectively, which are less than 15 cm away from the user's right and left pupils, respectively. The first thermal camera is configured to take thermal measurements of a first region of interest ($TH_{ROI1}$), where $ROI_1$ covers at least a portion of the right side of the user's forehead. The second thermal camera is configured to take thermal measurements of a second region of interest ($TH_{ROI2}$), where $ROI_2$ covers at least a portion of the user's left side of the forehead.

Figure 2:
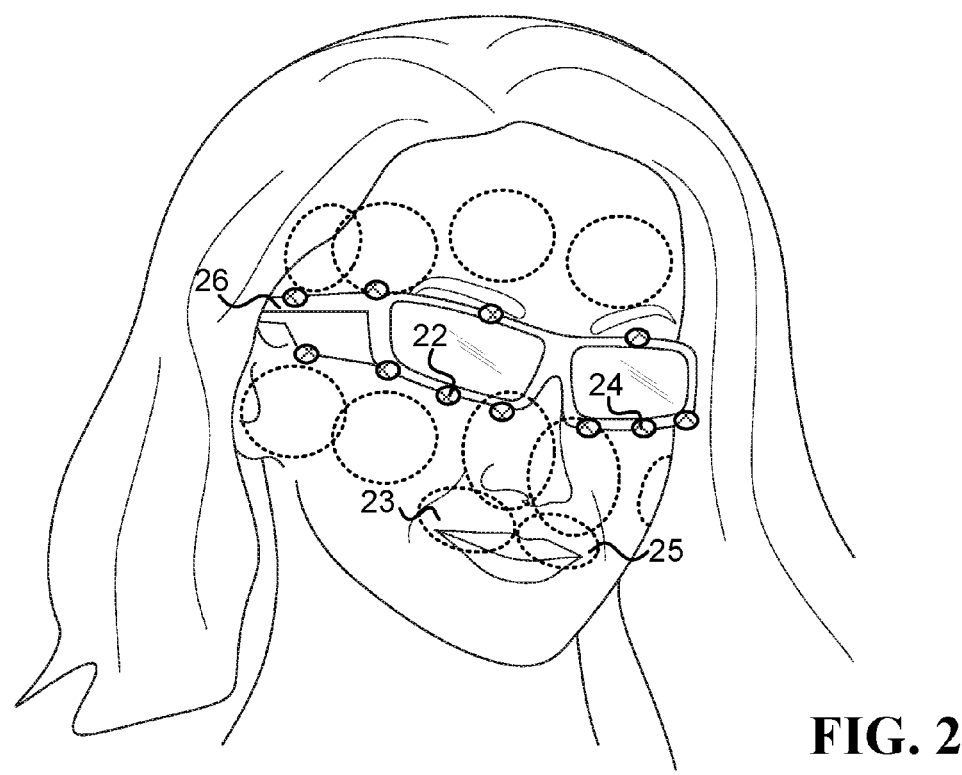
Figure 3:
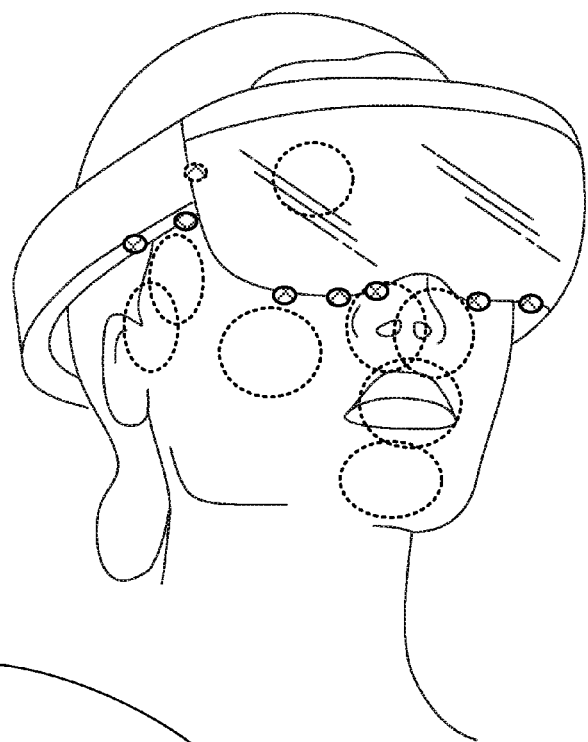
Figure 4:
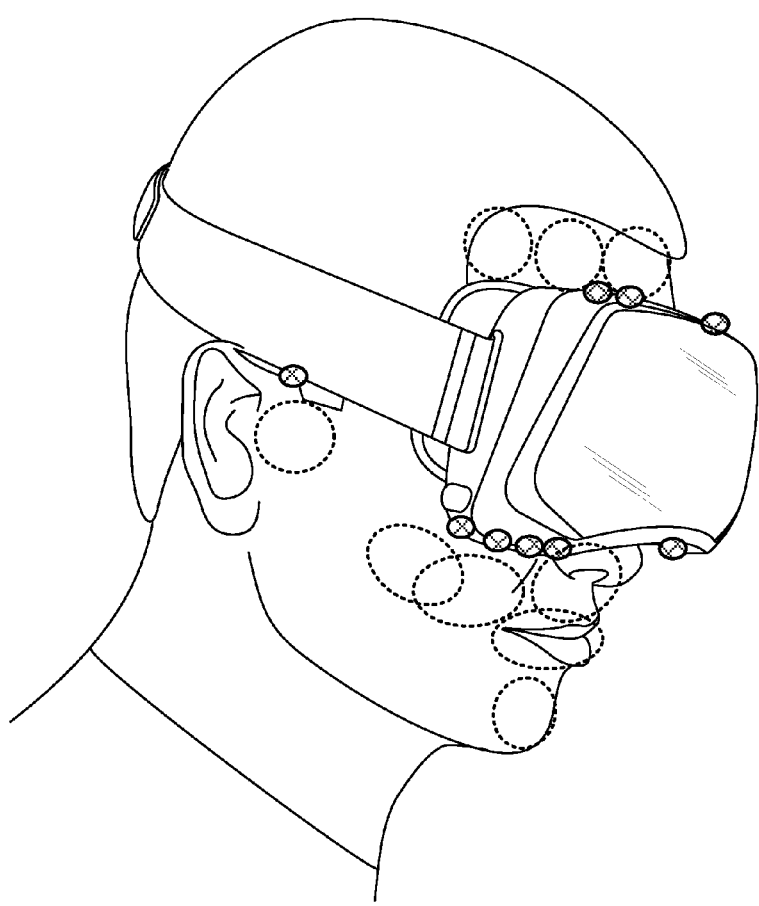

Referring to FIG. 2, the third thermal camera 22 and the fourth thermal camera 24 are physically coupled to the frame 26, at locations to the right and to the left of the symmetry axis, respectively, which are less than 15 cm away from the user's upper lip and below the first and second thermal cameras. The third thermal camera is configured to take thermal measurements of a third ROI ($TH_{ROI3}$), where $ROI_3$ 23 covers at least a portion of the user's right upper lip. The fourth thermal camera is configured to take thermal measurements of a fourth ROI ($TH_{ROI4}$), where $ROI_4$ 25 covers at least a portion of the user's left upper lip. Additionally, the third and fourth thermal cameras are located outside the exhale streams of the mouth and nostrils, and the thermal cameras are not in physical contact with their respective ROIs.

The system is configured to forward $TH_{ROI1}$, $TH_{ROI2}$, $TH_{ROI3}$, and $TH_{ROI4}$ to a processor configured to identify the physiological response. Optionally, the physiological response is indicative of an emotional state of the user. Optionally, the emotional state is indicative of an extent the user felt at least one of the following emotions: anger, disgust, fear, joy, sadness, and surprise. Additionally or alternatively, the physiological response may be indicative of a level of stress felt by the user. Additionally or alternatively, the physiological response may be indicative of an allergic reaction of the user. Additionally or alternatively, the physiological response may be indicative of a level of pain felt by the user.

In different embodiments, the ROIs mentioned above may cover slightly different regions on the user's face. In one embodiment, the overlap between $ROI_1$ and $ROI_2$ is below 50% of the smallest area from among the areas of $ROI_1$ and $ROI_2$, and the overlap between $ROI_3$ and $ROI_4$ is below 50% of the smallest area from among the areas of $ROI_3$ and $ROI_4$. In another embodiment, there is no overlap between $ROI_1$ and $ROI_2$, and there is no overlap between $ROI_3$ and $ROI_4$.

In one embodiment, the system described above may include a fifth thermal camera coupled to the frame, pointed at a fifth ROI ($ROI_5$), where $ROI_5$ covers at least a portion of the user's nose, and the fifth thermal camera is not in physical contact with $ROI_5$. In another embodiment, the system described above may include a fifth thermal camera coupled to the frame, pointed at a fifth ROI ($ROI_5$), where $ROI_5$ covers at least a portion of periorbital region of the user's face, and the fifth thermal camera is not in physical contact with $ROI_5$.

Some systems may include visible light cameras in addition to thermal cameras, as described in the following example. In one embodiment, a system configured to collect thermal and visible samples of a user's face from fixed relative positions includes at least a frame, a first thermal camera, a second thermal camera, and a visible light camera. The frame is configured to be worn on the user's head. The first thermal camera, the second thermal camera, and a visible light camera, are physically coupled to the frame. Furthermore, the thermal cameras and the visible light camera maintain fixed positioning relative to each other and relative to their corresponding ROIs when the user's head makes angular movements.

The first thermal camera is configured to take thermal measurements of a first region of interest ($TH_{ROI1}$), where $ROI_1$ covers at least part of the area around the user's eyes. The second thermal camera is configured to take thermal measurements of a second ROI ($TH_{ROI2}$), where $ROI_2$ covers at least part of the user's upper lip. The visible light camera is configured to take images of a third ROI ($IM_{ROI3}$), wherein $ROI_3$ covers at least part of the user's face.

In one embodiment, the system includes a processor configured to train a machine learning-based model for the user based on $TH_{ROI1}$ and $TH_{ROI2}$. Optionally, the model identifies an affective response of the user.

Herein, the term "visible light camera" refers to a camera designed to detect at least some of the visible spectrum. Examples of visible light sensors include active pixel sensors in complementary metal-oxide-semiconductor (CMOS), and semiconductor charge-coupled devices (CCD).

Following are some examples of systems that utilize thermal cameras for various applications.

FIG. 5 illustrates one embodiment of a wearable system, such as a head mounted system (HMS), configured to estimate a stress level. The system includes a frame, a thermal camera and circuit. The frame is configured to be worn on a user's head. The thermal camera is physically coupled to the frame at a position that is less than 15 cm away from one of the user's eyes, not in physical contact with the eye, and is configured to take thermal measurements of a region of interest ($TH_{ROI1}$), where the ROI covers at least part of a periorbital region of the user's eye. Locations 52, 53, and 54 in FIG. 5 illustrate possible positions for locating tiny thermal cameras for measuring the periorbital region around the right eye. The circuit 56, which may by wearable by the user or non-wearable, is configured to estimate the stress level of the user based on changes to temperature of the periorbital region received from the thermal camera. Optionally, the stress level relates to a stressful event, the delay between a stressful event and its representation on the at least part of the periorbital region is less than one minute, and most of the representation diminished within less than five minutes after the stressful event is over.

In one embodiment, the system described above includes an eye-tracking module coupled to the frame, which is configured to track gaze of the user. The wearable system is an optical see through head mounted display configured to operate in cooperation with a second camera configured to capture images of objects the user is looking at, and with a processor configured to match the objects the user is looking at with the stress levels inferred from the thermal measurements.

In one embodiment, the system described above includes a display that is coupled to the frame and is configured to present video comprising objects, and an eye-tracking module coupled to the frame and configured to track gaze of the user. The wearable system is configured to operate in cooperation with a processor configured to match the objects the user is looking at with the stress levels inferred from the thermal measurements.

Figure 8:
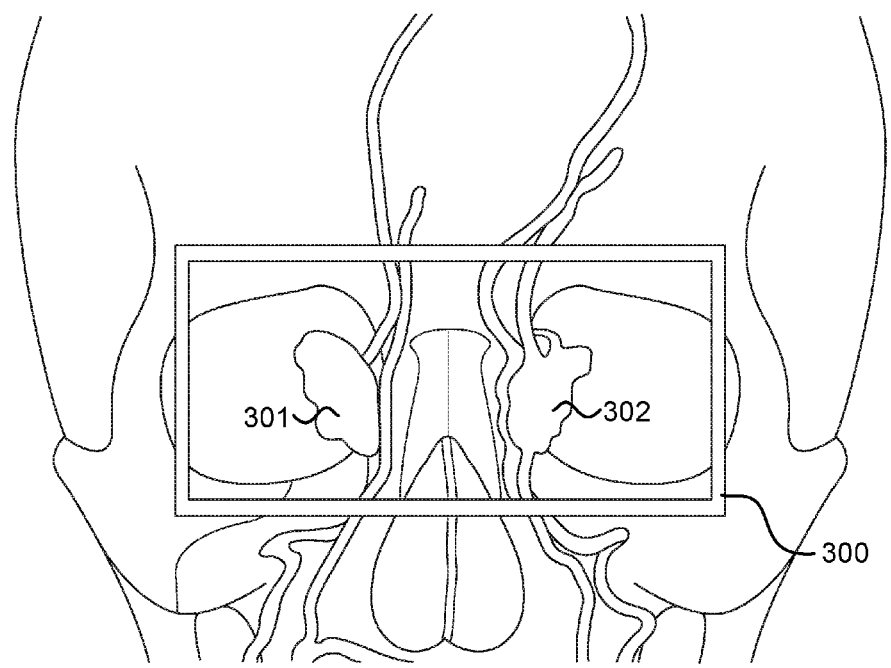
FIG. 8 illustrates the periorbital ROI.

The periorbital region of the user's face is discussed, for example, in the reference Tsiamyrtzis, P., Dowdall, J., Shastri, D., Pavlidis, I. T., Frank, M. G., & Ekman, P. (2007), "Imaging facial physiology for the detection of deceit", International Journal of Computer Vision, 71(2), 197-214. FIG. 8 illustrates the periorbital ROI, schematically represented by rectangle 300. Regions 301 and 302, referred to as the conduits in the eye corners, schematically represent about 10% of the hottest area within the periorbital ROI that may be sufficient to detect the "fight or flight" response during stress (also known as fight or flight syndrome).

The reference Pavlidis, I., Levine, J., & Baukol, P. (2000), "Thermal imaging for anxiety detection", In Computer Vision Beyond the Visible Spectrum: Methods and Applications, 2000. Proceedings. IEEE Workshop on (pp. 104-109). IEEE, also shows the periorbital region, together with the nasal area, right and left cheeks, chin area, and the neck area.

In another embodiment, a system configured to estimate a level of the fight or flight response of a user wearing a head mounted system (HMS) includes at least a frame, a thermal camera, and a circuit. The frame is configured to be worn on the head of the user. The thermal camera is physically coupled to the frame at a position that is less than 15 cm away from one of the user's eyes, is not in physical contact with the eye, and is configured to take thermal measurements of a region of interest ($TH_{ROI}$), wherein the ROI covers at least part of a periorbital region of the user's eye. The circuit is configured to estimate the level of fight or flight response of the user based on $TH_{ROI}$.

In one embodiment, the system described above includes a user interface configured to notify the user when the level of fight or flight response reaches a predetermined threshold. Optionally, the user interface utilizes at least one of an audio indication and visual indication to notify the user.

In one embodiment, the system described above includes: a display configured to show the user a video comprising objects, and a documenting module configured to save the estimated level of fight or flight response associated with the viewed objects.

In yet another embodiment, a system configured to estimate stress level of a user wearing a head mounted system (HMS) includes a frame, a thermal camera, and a circuit. The frame is configured to be worn on the head of the user. The thermal camera, which is physically coupled to the frame at a position that is less than 15 cm away from the tip of the user's nose, is configured to take thermal measurements of a region of interest ($TH_{ROI}$), wherein the ROI covers at least part of the area around the user's nose. Optionally, the thermal camera is based on at least one of: a thermopile sensor, and a pyroelectric sensor. One example of the region of interest around the nostrils is described in the reference Shastri, D., Papadakis, M., Tsiamyrtzis, P., Bass, B., & Pavlidis, I. (2012), "Perinasal imaging of physiological stress and its affective potential", Affective Computing, IEEE Transactions on, 3(3), 366-378. The circuit is configured to estimate the stress level based on $TH_{ROI}$.

In one embodiment, the system described above also includes a biofeedback mechanism configured to alert the user when the stress level reaches a predetermined threshold.

In still another embodiment, a wearable system configured to estimate a physiological response of a user includes a frame, first and second thermal cameras, and a circuit. The frame is configured to be worn on the head of the user. The first and second thermal cameras, physically coupled to the frame at positions that are less than 20 cm away from the user's forehead. The first thermal camera is configured to take thermal measurements of a first region of interest ($TH_{ROI1}$), where $ROI_1$ covers at least part of the right side of the user's forehead. The second thermal camera is configured to take thermal measurements of a second ROI ($TH_{ROI2}$), where $ROI_2$ covers at least part of the left side of the user's forehead. The circuit is configured to estimate the physiological response of the user based on $TH_{ROI1}$ and $TH_{ROI2}$. Optionally, THROI1 and THROI2 are correlated with blood flow in the frontal vessel of the user's forehead. Optionally, the physiological response is mental stress and the circuit is further configured to estimate frontal blood flow based on $TH_{ROI}$, which is indicative of mental stress. Optionally, the circuit is further configured to estimate periorbital perfusion based on $TH_{ROI}$, which is indicative of fight or flight response.

In one embodiment, the system described above includes a biofeedback mechanism configured to alert the user when the stress level reaches a predetermined threshold.

A head-mounted system (HMS) may utilize a thermal camera to estimate how a user feels towards digital content presented to the user, as the following example shows. Herein, "digital content" refers to any type of content that can be stored in a computer and presented by the computer to a use.

In one embodiment, a system configured to take thermal measurements of a user wearing a head mounted display (HMD) includes a display, a thermal camera, and a circuit. The display, which is worn by the user (e.g., it is attached to a frame of the HMS), is configured to present digital content to the user. The thermal camera, which is physically coupled to the HMD, is configured to take thermal measurements of a region of interest ($TH_{ROI}$) on the user's face; the thermal camera is not in physical contact with the ROI, and remains pointed at the ROI when the user's head makes angular movements. The circuit is configured to estimate affective response of the user to the digital content based on $TH_{ROI}$.

In one embodiment, the affective response is stress, the ROI covers at least part of the periorbital region of the user's face, and the greater the change in the ROI temperature the higher the stress level of the user. In another embodiment, the affective response is stress, the ROI covers at least part of the user's nose, and the magnitude of the stress is proportional to the change in the ROI temperature. In yet another embodiment, a value, from among $TH_{ROI}$, reaching a threshold is indicative of the affective response. In still another embodiment, at least one feature value utilized by a predictor that predicts occurrences of the affective response is based on $TH_{ROI}$.

In one embodiment, the system described above includes a computer configured to change the digital content presented to the user based on the estimated affective response.

In one embodiment, the thermal camera measures temperature at the ROI, and the system's nominal measurement error of the temperature at the ROI ($ERR_{TROI}$) is at least twice the system's nominal measurement error of the temperature change at the ROI ($ERR_{ATROI}$) when the user's head makes angular movements above 0.02 rad/sec. Additionally, wherein the circuit is able to identify affective response causing a temperature change at the ROI which is below $ERR_{TROI}$ and above $ERR_{\Delta TROI}$.

In another embodiment, the thermal camera measures temperature at the ROI, and the system's nominal measurement error of the temperature at the ROI ($ERR_{TROI}$) is at least five times the system's nominal measurement error of the temperature change at the ROI ($ERR_{\Delta TROI}$) when the user's head makes angular movements above 0.1 rad/sec. Additionally, the circuit is able to identify affective response causing a temperature change at the ROI which is below $ERR_{TROI}$ and above $ERR_{\Delta TROI}$.

Alertness, anxiety, and even fear appear to accompany people that are involved in illegal activities at the time of their action. Since those symptoms are produced by the sympathetic system, they cannot be totally controlled, and thus constitute a powerful biometric that is difficult to conceal. This biometric can provide valuable clues to security systems of critical/sensitive facilities/data about potential suspects immune to identification biometrics, such as first time offenders.

When a user experiences elevated feelings of alertness, anxiety, or fear, increased levels of adrenaline regulate blood flow. Redistribution of blood flow in superficial blood vessels causes abrupt changes in local skin temperature that is readily apparent in the user's face where the layer of flesh is very thin. The human face and body emit both in the mid-infrared (3-5 μm) and far-infrared (8-12 μm) bands, thus mid-infrared and far-infrared thermal sensors can sense this temperature variations in the face and trigger a process for detecting the illegal activity.

Following is a description of a security system designed to utilize thermal measurements of a user's face in order to detect irregular activity. In one embodiment, the user is permitted to access sensitive data only through an HMD equipped with a thermal camera that measures temperature variations on the user's face while he/she is accessing the sensitive data. This way the user is under surveillance each time he/she is accessing the sensitive data, and optionally there is no way for the user to access the sensitive data without being monitored by the security system.

In one embodiment, the security system configured to detect an irregular activity includes a head mounted display (HMD) that includes: a frame, a display module, and a thermal camera. The thermal camera is configured to take thermal measurements of a region of interest ($TH_{ROI}$) on the user's face; the thermal camera is not in physical contact with the ROI and remains pointed at the ROI when the user's head makes angular movements. Optionally, the ROI covers at least part of periorbital region of the user's face. Optionally, the thermal camera comprises an uncooled thermal sensor.

A circuit (e.g., a processor) is configured to calculate a baseline thermal profile for the user based on readings of $TH_{ROI}$ taken while the user watches baseline sensitive data presented on the display module. The circuit is further configured to calculate a certain thermal profile for the user based on readings of $TH_{ROI}$ taken while the user watches a certain sensitive data presented on the display module, and issue an alert when the difference between the certain thermal profile and the baseline thermal profile reaches a predetermined threshold.

In one embodiment, $TH_{ROI}$ is expressed as temperature at the ROI, and the baseline thermal profile expresses ordinary temperature at the ROI while the user is exposed to sensitive data. In another embodiment, $TH_{ROI}$ is expressed as temperature change at the ROI, and the baseline thermal profile expresses ordinary temperature changes at the ROI around the time of switching from being exposed to non-sensitive data to being exposed to sensitive data. In still another embodiment, $TH_{ROI}$ is expressed as temperature change at the ROI, and the baseline thermal profile expresses ordinary temperature change at the ROI around the time of switching from being exposed to sensitive data to being exposed to non-sensitive data.

In one embodiment, the alert relates to detection of an illegal activity. Optionally, the delay between the time of performing the illegal activity and the time of reaching the predetermined threshold is less than two minutes.

In another embodiment, the security system utilizes the alert to estimate job burnout; the greater the difference between the certain thermal profile and the baseline thermal profile the worse is the job burnout.

In one embodiment, the user watches the certain sensitive data within less than 15 minutes before or after watching the baseline sensitive data. In some cases, it may be useful to compare close events because the shorter the time between watching the baseline sensitive data and watching the certain sensitive data, the smaller the negative effect of environmental changes and normal physiological changes may be. In one example, the user watches the certain sensitive data immediately before and/or after watching the baseline sensitive data. In another example, the user watches the certain sensitive data within less than 5 minutes before and/or after watching the baseline sensitive data.

When the user observes data over period of time, in some embodiments, each segment of data (e.g., data observed during a certain span of a few minutes) may serve both as a baseline sensitive data (for a certain evaluation) and as the certain sensitive data (for another evaluation).

In one embodiment, the circuit is further configured to receive characteristics of the environment the user is in while watching the certain sensitive data, and further configured to select for the baseline an event where the user watched the baseline sensitive data while being in a similar environment. In one example, the difference in ambient temperatures of similar environments is less than 2 degrees. In another example, the difference in humidity of similar environments is less than 5 percent. In still another example, the difference in oxygen percent in the air of similar environments is less than 2 percent.

In one embodiment, the security system further detects that the user moved the HMD while being exposed to the certain sensitive data, and therefore does not allow the user to perform a certain transaction related to the certain sensitive data. In one example, the certain transaction comprises at least one of the following: copying, reading, and modifying the certain sensitive data. In another example, the certain sensitive data relates to money, and the certain transaction comprises electronic funds transfer from one person or entity to another person or entity.

In another embodiment, the security system further detects that the user moved the HMD while being exposed to the certain sensitive data, and marks the relationship between the user and the certain sensitive data as being suspicious. Optionally, the security system issues a security alert after detecting that the user moved again the HMS while being exposed to another sensitive data that is of the same type as the certain sensitive data.

Figure 12:
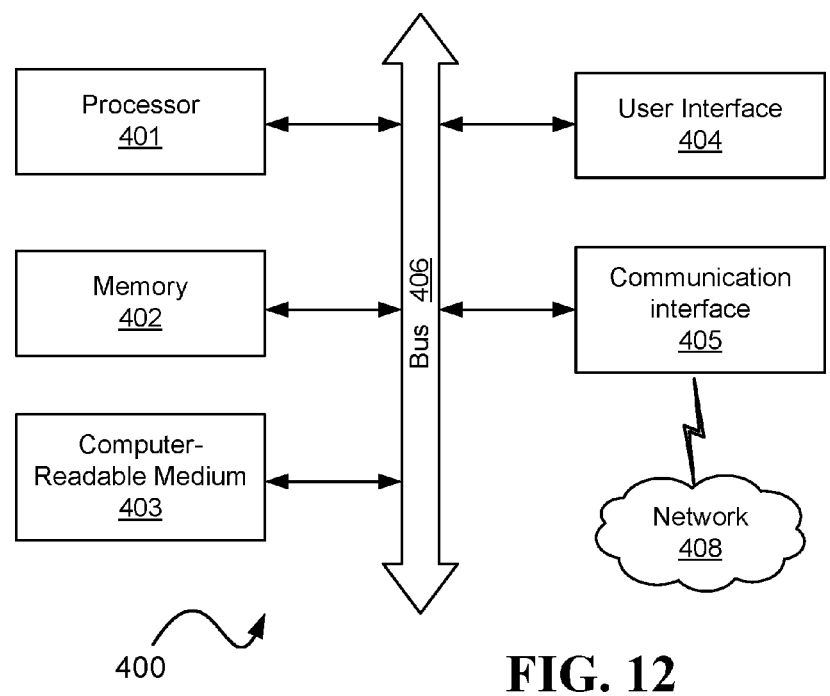
FIG. 12 is a schematic illustration of a computer able to realize one or more of the embodiments discussed herein.

FIG. 12 is a schematic illustration of a computer 400 that is able to realize one or more of the embodiments discussed herein. The computer 400 may be implemented in various ways, such as, but not limited to, a server, a client, a personal computer, a set-top box (STB), a network device, a handheld device (e.g., a smartphone), computing devices embedded in wearable devices (e.g., a smartwatch or a computer embedded in clothing), computing devices implanted in the human body, and/or any other computer form capable of executing a set of computer instructions. Further, references to a computer include any collection of one or more computers that individually or jointly execute one or more sets of computer instructions to perform any one or more of the disclosed embodiments.

The computer 400 includes one or more of the following components: processor 401, memory 402, computer readable medium 403, user interface 404, communication interface 405, and bus 406. In one example, the processor 401 may include one or more of the following components: a general-purpose processing device, a microprocessor, a central processing unit, a complex instruction set computing (CISC) microprocessor, a reduced instruction set computing (RISC) microprocessor, a very long instruction word (VLIW) microprocessor, a special-purpose processing device, an application specific integrated circuit (ASIC), a field programmable gate array (FPGA), a digital signal processor (DSP), a distributed processing entity, and/or a network processor. Continuing the example, the memory 402 may include one or more of the following memory components: CPU cache, main memory, read-only memory (ROM), dynamic random access memory (DRAM) such as synchronous DRAM (SDRAM), flash memory, static random access memory (SRAM), and/or a data storage device. The processor 401 and the one or more memory components may communicate with each other via a bus, such as bus 406.

Still continuing the example, the communication interface 405 may include one or more components for connecting to one or more of the following: LAN, Ethernet, intranet, the Internet, a fiber communication network, a wired communication network, and/or a wireless communication network. Optionally, the communication interface 405 is used to connect with the network 408. Additionally or alternatively, the communication interface 405 may be used to connect to other networks and/or other communication interfaces. Still continuing the example, the user interface 404 may include one or more of the following components: (i) an image generation device, such as a video display, an augmented reality system, a virtual reality system, and/or a mixed reality system, (ii) an audio generation device, such as one or more speakers, (iii) an input device, such as a keyboard, a mouse, a gesture based input device that may be active or passive, and/or a brain-computer interface.

At least some of the methods described in this disclosure, which may also be referred to as "computer-implemented methods", are implemented on a computer, such as the computer 400. When implementing a method from among the at least some of the methods, at least some of the steps belonging to the method are performed by the processor 401 by executing instructions. Additionally, at least some of the instructions for running methods described in this disclosure and/or for implementing systems described in this disclosure may be stored on a non-transitory computer-readable medium.

Herein, a predetermined value, such as a predetermined confidence level or a predetermined threshold, is a fixed value and/or a value determined any time before performing a calculation that compares a certain value with the predetermined value. A value is also considered to be a predetermined value when the logic, used to determine whether a threshold that utilizes the value is reached, is known before start of performing computations to determine whether the threshold is reached.

In this description, references to "one embodiment" mean that the feature being referred to may be included in at least one embodiment of the invention. Moreover, separate references to "one embodiment" or "some embodiments" in this description do not necessarily refer to the same embodiment. Additionally, references to "one embodiment" and "another embodiment" may not necessarily refer to different embodiments, but may be terms used, at times, to illustrate different aspects of an embodiment.

The embodiments of the invention may include any variety of combinations and/or integrations of the features of the embodiments described herein. Although some embodiments may depict serial operations, the embodiments may perform certain operations in parallel and/or in different orders from those depicted. Moreover, the use of repeated reference numerals and/or letters in the text and/or drawings is for the purpose of simplicity and clarity and does not in itself dictate a relationship between the various embodiments and/or configurations discussed. The embodiments are not limited in their applications to the details of the order or sequence of steps of operation of methods, or to details of implementation of devices, set in the description, drawings, or examples. Moreover, individual blocks illustrated in the figures may be functional in nature and therefore may not necessarily correspond to discrete hardware elements. In the claims, the terms "first", "second" and so forth are to be interpreted merely as ordinal designations, and shall not be limited in themselves.

While the methods disclosed herein have been described and shown with reference to particular steps performed in a particular order, it is understood that these steps may be combined, sub-divided, and/or reordered to form an equivalent method without departing from the teachings of the embodiments. Accordingly, unless specifically indicated herein, the order and grouping of the steps is not a limitation of the embodiments. Furthermore, methods and mechanisms of the embodiments will sometimes be described in singular form for clarity. However, some embodiments may include multiple iterations of a method or multiple instantiations of a mechanism unless noted otherwise. For example, when a processor is disclosed in one embodiment, the scope of the embodiment is intended to also cover the use of multiple processors. Certain features of the embodiments, which may have been, for clarity, described in the context of separate embodiments, may also be provided in various combinations in a single embodiment. Conversely, various features of the embodiments, which may have been, for brevity, described in the context of a single embodiment, may also be provided separately or in any suitable sub-combination. Embodiments described in conjunction with specific examples are presented by way of example, and not limitation. Moreover, it is evident that many alternatives, modifications, and variations will be apparent to those skilled in the art. It is to be understood that other embodiments may be utilized and structural changes may be made without departing from the scope of the embodiments. Accordingly, this disclosure is intended to embrace all such alternatives, modifications, and variations that fall within the spirit and scope of the appended claims and their equivalents.

What is claimed is:

1. A system comprising:
   first and second thermal cameras physically coupled to a frame configured to be worn on a user's head;

the first thermal camera is configured to take thermal measurements of a first region of interest ($TH_{ROI1}$), wherein $ROI_1$ covers at least a portion of the right side of the user's forehead, the first thermal camera is located below $ROI_1$, and the first thermal camera does not occlude $ROI_1$; and the second thermal camera is configured to take thermal measurements of a second ROI ($TH_{ROI2}$), wherein $ROI_2$ covers at least a portion of the left side of the user's forehead, the second thermal camera is located below $ROI_2$, and the second thermal camera does not occlude $ROI_2$;

wherein the overlap between $ROI_1$ and $ROI_2$ is below 80% of the smallest area from among the areas of $ROI_1$ and $ROI_2$, and as a result of being coupled to the frame, the thermal cameras remain pointed at their corresponding ROIs when the user's head makes angular movements.

2. The system of claim 1, wherein the first and second thermal cameras are based on thermopile sensors.

3. The system of claim 1, wherein the first and second thermal cameras are based on pyroelectric sensors.

4. The system of claim 1, wherein the system is configured to forward $TH_{ROI1}$ and $TH_{ROI2}$ to a processor configured to identify a physiological response based on $TH_{ROI1}$ and $TH_{ROI2}$.

5. The system of claim 4, wherein the physiological response is indicative of at least one of the following: stress, mental workload, fear, sexual arousal, anxiety, pain, pulse, headache, and stroke.

6. The system of claim 1, wherein the right side of the user's forehead covers at least 30% of $ROI_1$, and the left side of the user's forehead covers at least 30% of $ROI_2$.

7. The system of claim 1, wherein the right side of the user's forehead covers at least 80% of $ROI_1$, and the left side of the user's forehead covers at least 80% of $ROI_2$.

8. The system of claim 1, wherein the first and second thermal cameras measure temperatures at $ROI_1$ and $ROI_2$, respectively; and further comprising a circuit configured to: receive a series of temperature measurements at $ROI_1$ and calculate temperature changes at $ROI_1$ ($\Delta T_{ROI1}$), receive a series of temperature measurements at $ROI_2$ and calculate temperature changes at $ROI_2$ ($\Delta T_{ROI2}$), and utilize $\Delta T_{ROI1}$ and $\Delta T_{ROI2}$ to identify a physiological response.

9. The system of claim 8, wherein the system's nominal measurement error of the temperatures at $ROI_1$ is at least twice the system's nominal measurement error of the temperature changes at $ROI_1$ when the user's head makes angular movements above 0.02 rad/sec.

10. The system of claim 9, wherein the system's nominal measurement error of the temperatures at $ROI_1$ is at least five time the system's nominal measurement error of the temperature changes at $ROI_1$ when the user's head makes angular movements above 0.2 rad/sec.

11. A system comprising:
first and second thermal cameras physically coupled to a frame configured to be worn on a user's head;
the first thermal camera is configured to take thermal measurements of a first region of interest ($TH_{ROI1}$), wherein $ROI_1$ covers at least a portion of the right side frontal superficial temporal artery of the user; and
the second thermal camera is configured to take thermal measurements of a second region of interest ($TH_{ROI2}$), wherein $ROI_2$ covers at least a portion of the left side frontal superficial temporal artery of the user;
wherein the first and second thermal cameras are not in physical contact with their corresponding ROIs, and as a result of being coupled to the frame, the thermal cameras remain pointed at their corresponding ROIs when the user's head makes angular movements.

12. The system of claim 11, wherein the system is configured to forward $TH_{ROI1}$ and $TH_{ROI2}$ to a processor configured to identify a physiological response based on $TH_{ROI1}$ and $TH_{ROI2}$.

13. The system of claim 12, wherein the physiological response is indicative of the user's arterial pulse.

14. The system of claim 12, wherein the physiological response is indicative of at least one of the following: stress, mental workload, fear, anxiety, pain, headache, and stroke.

15. The system of claim 11, wherein the first and second thermal cameras are based on thermopile sensors.

16. The system of claim 11, wherein the first and second thermal cameras are based on pyroelectric sensors.

17. A system comprising:
first and second thermal cameras physically coupled to a frame configured to be worn on a user's head;
the first thermal camera is configured to take thermal measurements of a first region of interest ($TH_{ROI1}$), wherein $ROI_1$ covers at least a portion of the right side superficial temporal artery of the user; and
the second thermal camera is configured to take thermal measurements of a second region of interest ($TH_{ROI2}$), wherein $ROI_2$ covers at least a portion of the left side superficial temporal artery of the user;
wherein the first and second thermal cameras are not in physical contact with their corresponding ROIs, and as a result of being coupled to the frame, the thermal cameras remain pointed at their corresponding ROIs when the user's head makes angular movements.

18. The system of claim 17, wherein the system is configured to forward $TH_{ROI1}$ and $TH_{ROI2}$ to a processor configured to identify a physiological response based on $TH_{ROI1}$ and $TH_{ROI2}$.

19. The system of claim 18, wherein the physiological response is indicative of the user's arterial pulse.

20. The system of claim 18, wherein the physiological response is indicative of at least one of the following: stress, mental workload, fear, anxiety, pain, headache, and stroke.

* * * * *